United States Patent
Musgrave et al.

[11] Patent Number: 5,875,532
[45] Date of Patent: Mar. 2, 1999

[54] SURGICAL INSTRUMENT BLADE INJECTOR AND MOUNTING METHOD

[75] Inventors: Alford D. Musgrave, 1850 Jeffrey Ave., Escondido, Calif. 92027-4441; Ulysses S.A. Brown, Escondido, Calif.

[73] Assignee: Alford D. Musgrave, Escondido, Calif.

[21] Appl. No.: 522,143

[22] Filed: Aug. 31, 1995

[51] Int. Cl.⁶ .................................................. B23P 19/04
[52] U.S. Cl. ............................ 29/239; 206/355; 269/16
[58] Field of Search ............................ 29/235, 239, 242; 206/355; 269/1, 3, 16

[56] References Cited

U.S. PATENT DOCUMENTS

| | | |
|---|---|---|
| 4,244,094 | 1/1981 | Rucinski . |
| 4,386,457 | 6/1983 | Coombs . |
| 4,395,807 | 8/1983 | Eldridge, Jr. et al. . |
| 4,466,539 | 8/1984 | Frauenhoffer . |
| 4,730,376 | 3/1988 | Yamada . |
| 4,903,390 | 2/1990 | Vidal et al. . |
| 5,088,173 | 2/1992 | Kromer et al. . |
| 5,255,422 | 10/1993 | Russo et al. . |
| 5,667,067 | 9/1997 | Gabriel .................................... 29/239 |

*Primary Examiner*—P. W. Echols
*Attorney, Agent, or Firm*—Brown, Martin, Haller & McClain

[57] ABSTRACT

A device and method for injecting a blade onto a surgical instrument and extracting a blade from a surgical instrument. The injector includes a housing having an elongated cavity for receiving the instrument head. Prior to injection, a blade is retained in the cavity. To inject a blade, a user inserts the instrument head into the channel. The rim of the blade aperture engages the groove on the tang as the instrument is inserted. When the tang is fully engaged with blade, the user can withdraw the instrument with the blade mounted on it. The extractor includes a housing having an elongated cavity for receiving the instrument head. The channel has a slot that extends through the housing. A spring catch is mounted in the cavity on a side wall opposite the spring clip. To extract a blade, a user inserts the instrument head into the channel until the spring catch engages the proximal end of the blade. The user then angles the instrument handle away from the spring catch and withdraws the instrument handle from the channel while the spring catch retains the blade in the housing. When the blade is fully separated from the instrument head, the blade falls through the slot into an integral receptacle for disposal.

8 Claims, 2 Drawing Sheets

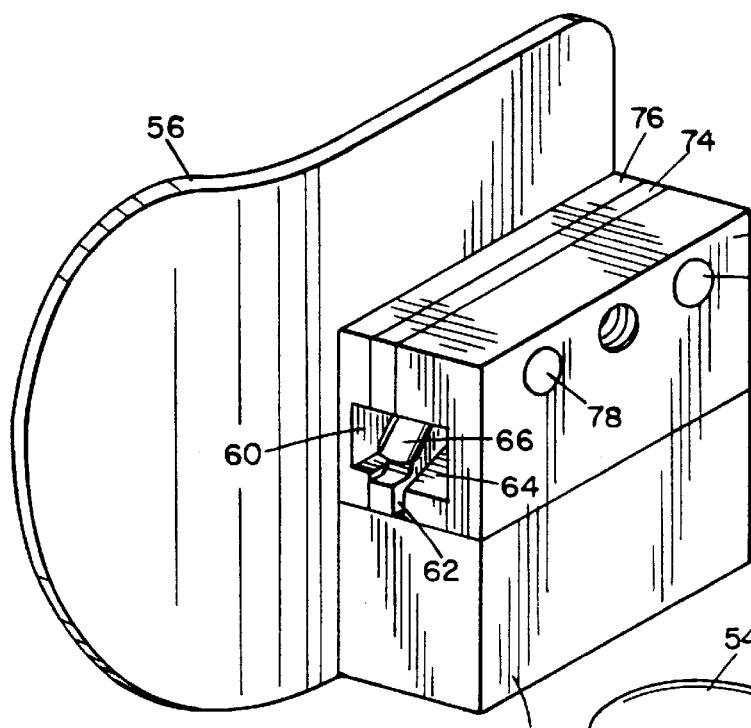
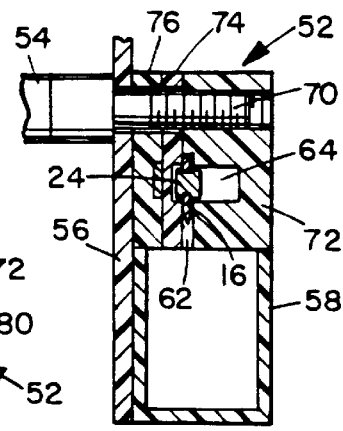
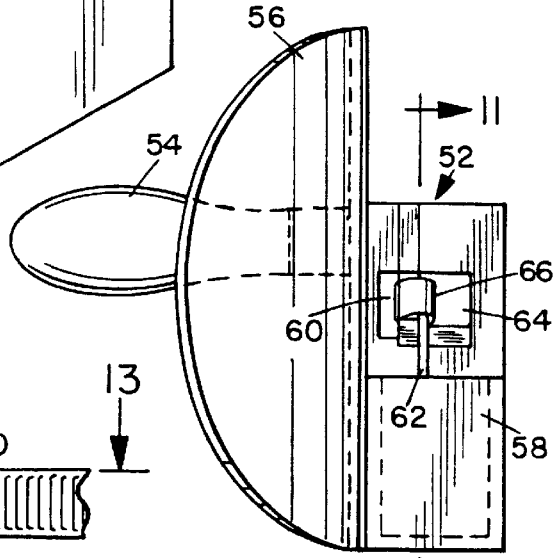
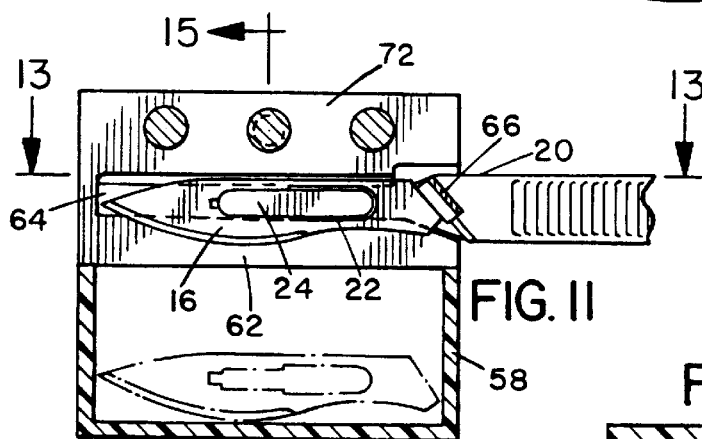
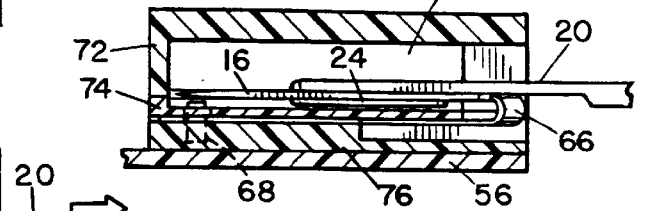
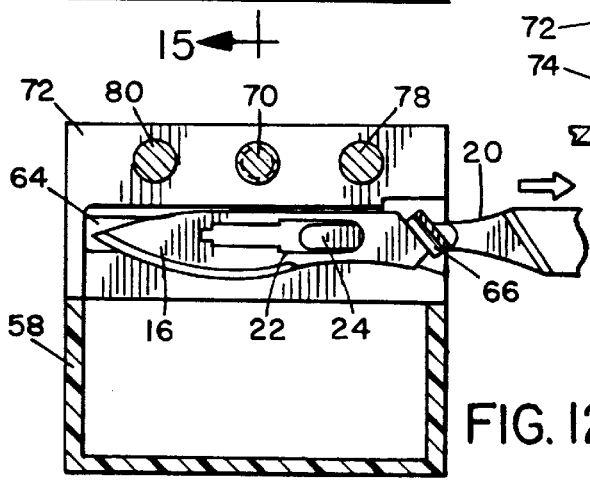
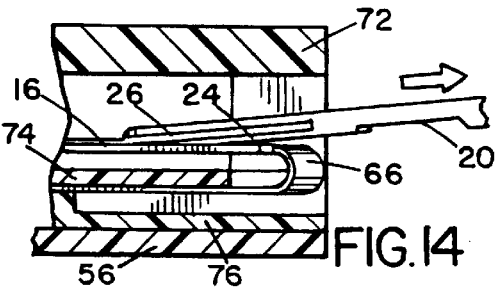

SURGICAL INSTRUMENT BLADE INJECTOR AND MOUNTING METHOD

BACKGROUND OF THE INVENTION

The present invention relates to a device that manipulates a blade on the head of a scalpel. Infectious diseases can be transmitted from a used scalpel blade to a surgeon if the surgeon is accidentally cut while removing the blade from the scalpel head with his or her fingers. Although surgeons have always been concerned about accidentally lacerating themselves, the problem has become a grave one with the advent of AIDS and other, as yet incurable, diseases that are communicated via infected blood and tissues.

A scalpel blade has an elongated shape and a sharp edge and point. The blade also has an elongated aperture into which a correspondingly elongated boss or tang on the scalpel head fits to secure the two together. The aperture is wider at its rear or proximal end than at its forward or distal end. The tang has grooves on its upper and lower edges that engage the upper and lower rims of the narrower portion of the blade aperture, thereby preventing the blade from moving laterally on the tang. To remove a scalpel blade from the scalpel head in the time-honored manner, the surgeon grasps the (unsharpened) heel of the blade with two fingers and bends it away from the scalpel head slightly. The heel typically has an indentation on one or both edges to facilitate grasping it between the fingers. With the proximal end of the blade thus bent, the proximal end of blade aperture clears the proximal end of the tang on the scalpel head. The surgeon then grasps the blade heel with two fingers and moves the blade forward with respect to the scalpel head, with the aperture rim sliding in the groove on the tang. When the tang has been completely removed from the aperture, the surgeon may place the blade in a receptacle for scalpel blades and similar sharp objects for disposal. If the surgeon accidentally loses his or her grip on the blade while moving the blade forward, however, the surgeon's finger may slip over the sharp edge, lacerating it. A surgeon may also be accidentally lacerated while mounting a blade on a surgical instrument.

Practitioners in the art have developed devices that allow a surgeon to extract a scalpel blade without grasping the heel of the blade between the fingers. Nevertheless, these devices may require a surgeon to use both hands to operate them. These devices may also not fully sequester the blade in a receptacle after removal. Moreover, many of these devices are not economical to manufacture. It would be desirable to provide a blade extractor and injector that are simple and convenient to use and economical to manufacture. These problems and deficiencies are clearly felt in the art and are solved by the present invention in the manner described below.

SUMMARY OF THE INVENTION

The present invention is an apparatus for manipulating a surgical blade on the head of a surgical instrument such as a scalpel. The apparatus comprises a housing having a cavity for receiving the instrument head and blade.

In one aspect, the present invention comprises an injector apparatus for injecting a blade onto an instrument handle. The injector comprises a housing having an elongated cavity for receiving the distal or head end of the instrument handle. Prior to injection, a blade is retained in the cavity inside the housing. The cavity may be sealed with a breakable barrier to prevent contamination of a sterile blade. To inject a blade, a user inserts the instrument head into the cavity. The aperture rim engages the groove on the instrument head as the instrument handle is inserted. The upper and lower blade aperture rims thus slide in the upper and lower grooves in the instrument head until the blade and instrument head are fully engaged. The user can then withdraw the instrument handle with the blade mounted on it from the cavity.

In another aspect, the present invention comprises an extractor apparatus for extracting a blade from an instrument handle. The extractor comprises a housing having an elongated cavity for receiving the distal or head end of the instrument handle. A spring catch is mounted in the cavity. To extract a blade, a user inserts the instrument head into the cavity and then angles it away from the spring catch. Because the blade is retained against lateral movement in the cavity, the proximal end of the blade tends to separate from the instrument head when the user angles the instrument handle. This separation disengages the proximal or heel portion of the instrument blade from the instrument head. The spring catch engages the proximal end of the blade as the handle separates from the blade. With the instrument handle in this angled orientation and the spring catch engaging the blade, the user withdraws the instrument handle from the cavity. The spring catch retains the blade in the housing while the user withdraws the instrument handle. The upper and lower blade aperture rims thus slide in the upper and lower grooves in the instrument head until the blade and instrument head are fully disengaged.

The present invention allows a user to inject an instrument blade onto an instrument handle or extract an instrument blade from an instrument handle without handling the blade. The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated in the accompanying drawings, wherein:

FIG. 9 is a perspective view of the blade extractor;

FIG. 10 is a front end view of the blade extractor;

FIG. 11 is a sectional view taken along line 11—11 of FIG. 10, with a scalpel head and blade inserted in the extractor;

FIG. 12 is a view similar to FIG. 11, showing withdrawal of the scalpel head and extraction of the blade;

FIG. 13 is a sectional view taken along line 13—13 of FIG. 11;

FIG. 14 is an enlarged view of a portion of FIG. 13, showing retention of the blade as the scalpel head is withdrawn; and FIG. 15 is a sectional view taken along line 15—15 of FIG. 11.

DESCRIPTION OF PREFERRED EMBODIMENTS

Figure 1:
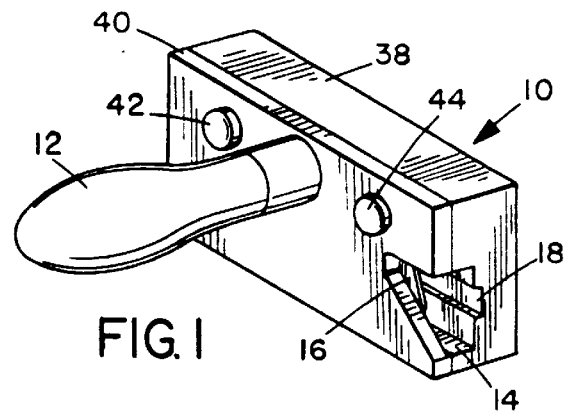
FIG. 1 is a perspective view of the blade injector.

As illustrated in FIG. 1, a blade injector comprises a housing 10 and a handle 12. Housing 10 has a cavity 14. Prior to injection, a blade 16 is retained in cavity 14. A desiccating tissue wrapper (not shown) may be disposed in cavity 14 in any suitable manner, such as wrapped around blade 16, to inhibit corrosion. A channel 18 formed in a side wall of cavity 14 is angled with respect to blade 16 to guide the instrument head 20 during injection, as described below. Cavity 14 is defined by channel 18 and the slot-like portion in which blade 16 is retained.

Figure 2:
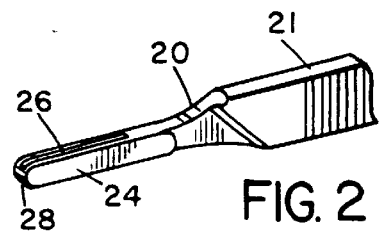
FIG. 2 is a perspective view of a typical scalpel head.
Figure 3:
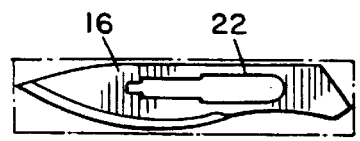
FIG. 3 is a side elevation view of a typical blade as retained in the blade injector prior to injection.
Figure 4:
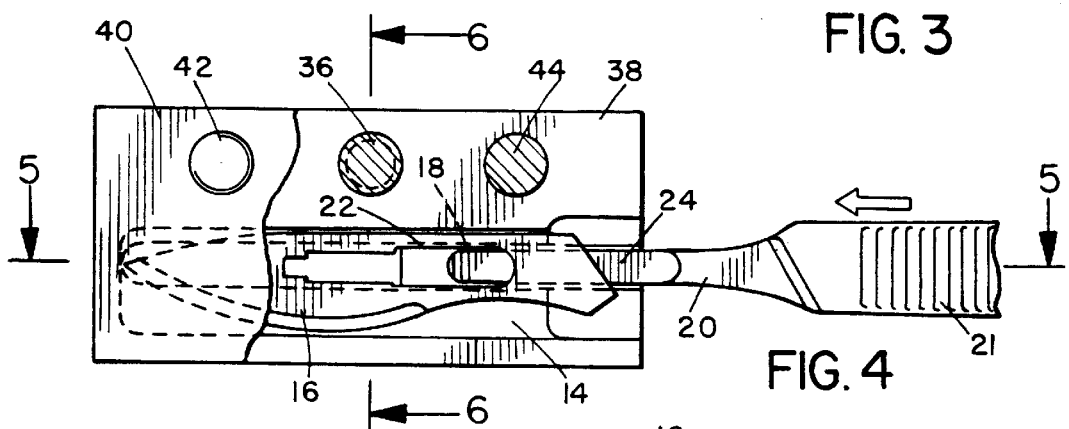
FIG. 4 is an enlarged side elevation view of the blade injector, partially cut away to show insertion of the scalpel head.
Figure 5:
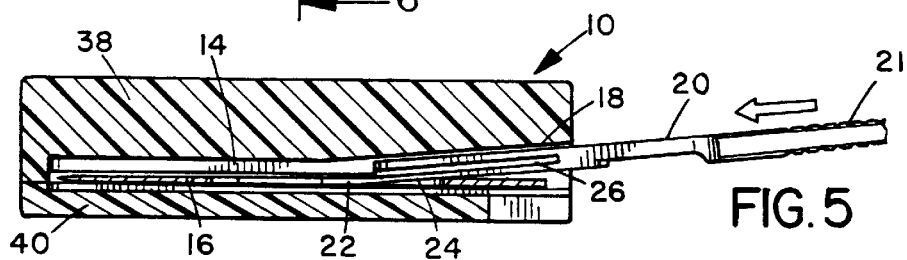
FIG. 5 is a sectional view taken along line 5—5 of FIG. 4.
Figure 7:
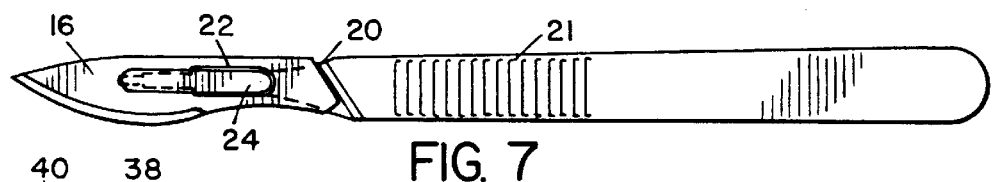
FIG. 7 is a side elevation view of the scalpel head with the blade mounted thereon.
Figure 6:
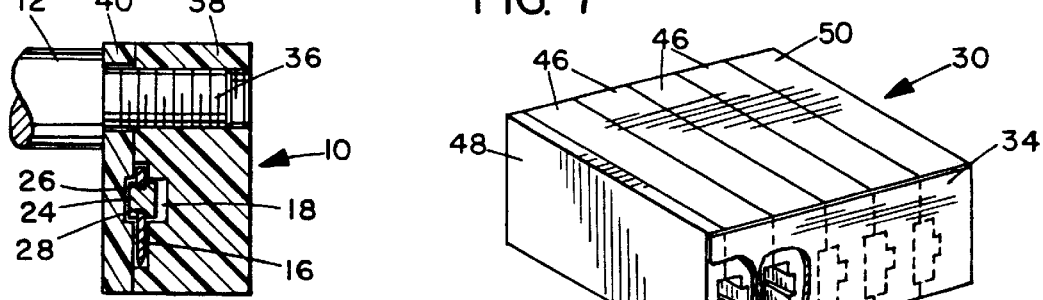
FIG. 6 is a sectional view taken along line 6—6 of FIG. 4.

To inject blade 16, i.e., to mount blade 16 on instrument head 20, a user grasps the instrument handle 21 and inserts instrument head 20 into cavity 14 such that it is guided in channel 18, as shown in FIGS. 4 and 5. As illustrated in FIG. 3, blade 16 has an aperture 22 that is wider at the proximal end of blade 16 than at the distal end of blade 16. As instrument head 20 is inserted, guided by channel 18, the tang 24 of instrument head enters the wider portion of aperture 22. As best illustrated in FIG. 2, tang 24 has grooves 26 and 28 along its upper and lower sides, respectively. Returning to FIGS. 4 and 5, as instrument head 20 is further inserted, still guided by channel 18, the upper and lower rims of the narrow portion of aperture 22 slide into grooves 26 and 28, respectively. When tang 24 is fully engaged in aperture 22 in this manner, the user may withdraw instrument head 20 from cavity 14, with blade 16 mounted on instrument head 20 as shown in FIG. 7.

Figure 8:
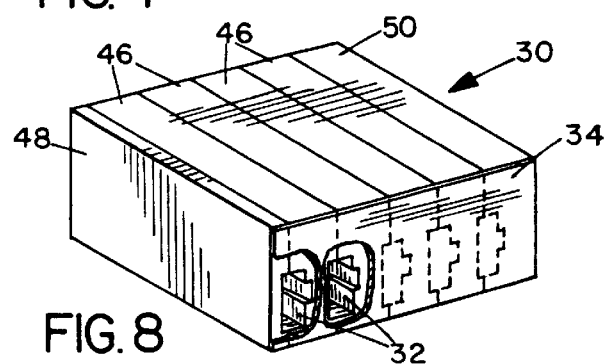
FIG. 8 is a perspective view of an alternative injector.

As illustrated in FIG. 8, an alternative blade injector comprises a housing 30 having multiple cavities 32, each constructed and used to inject a blade as described above with respect to the embodiment illustrated in FIGS. 1–6. A barrier or seal 34 covers the ends of cavities 32. Cavities 32 and the blades retained therein (not shown) are sterilized during manufacturing, and seal 34 prevents subsequent contamination. Seal 34 is preferably breakable, but it may alternatively be removable. When the user inserts instrument head 20 into one of cavities 34, the distal end breaks or punctures the portion of seal 34 covering it.

Housings 10 and 30 are preferably made of plastic because it is economical, but may be made of stainless steel, anodized aluminum or any other suitable material. Although a handle 12 may be included in certain embodiments, as exemplified by that illustrated in FIGS. 1–6, it is not necessary. In the embodiment illustrated in FIGS. 1–6 handle 12 has a threaded end 36 that holds together two halves 38 and 40 that housing 10 comprises. Two pegs 42 and 44, each having an end secured in half 38, extend through corresponding openings in half 40 to align halves 38 and 40 during assembly. In the embodiment illustrated in FIG. 8, to facilitate economical assembly, housing 30 comprises multiple interior sections 46, each having a left and right side wall portion of a cavity 32, a left end section 48 having only the left side wall portion of a cavity 32, and a right end section 50 having only the right side wall portion of a cavity 32. Nevertheless, housings 10 and 30 may have any suitable construction.

As illustrated in FIGS. 9–15, a blade extractor comprises a housing 52, a handle 54, a guard 56, and a blade receptacle 58. Housing 52 has a cavity 60. A slot 62 in housing 52 defines a passageway between cavity 60 and the interior of blade receptacle 58. A channel 64 is formed in a side wall of cavity 60 to guide instrument head 20 (see FIG. 7) during blade extraction, as described below. A spring catch 66 is disposed in cavity 60 and retained at its distal end by a peg 68 (FIG. 13). The proximal end of spring catch 66 is curved or hooked. Spring catch 66 is made of a suitable resilient material such as sheet stainless steel.

To extract blade 16, i.e., to remove blade 16 from instrument head 20, a user grasps instrument handle 21 and inserts instrument head 20, (with blade 16 mounted thereon) into cavity 60 such that blade 16 deflects the proximal end of spring catch 66 and enters slot 62, as shown in FIG. 11. Instrument head 20 is guided in channel 64. When instrument head 20 is fully inserted in cavity 60, the hooked end of spring catch 66 catches on the proximal end of blade 16, as shown in FIG. 11. The user then angles instrument handle 21 in a direction away from spring catch 66. Because blade 16 is retained against lateral movement in slot 62, the proximal end of tang 24 disengages the wider portion of aperture 22. The user then withdraws instrument head 20 from cavity 60, as shown in FIGS. 12–14. Because spring catch 66 is caught on the proximal end of blade 16, blade 16 is retained while the upper and lower rims of the narrow portion of aperture 22 slide out of grooves 26 and 28, respectively. When instrument head 20 is completely disengaged from aperture 22, blade 16 falls through slot 62 into the interior of receptacle 58 for disposal, as shown in FIG. 11. Receptacle 58 may be removably connected to housing 52 to facilitate disposal of the removed blades.

Housing 52, handle 54 and receptacle 58 may be made of any suitable material, such as plastic, stainless steel or anodized aluminum. Guard 56 is preferably made of clear LEXAN® polycarbonate plastic.

Although a handle 54 and guard 56 are preferably included for portable hand-held operation, housing 52 may alternatively be mounted in a permanent or semi-permanent location. In the illustrated embodiment handle 54 has a threaded end 70 that holds together the three portions 72, 74 and 76 that housing 52 comprises. Two pegs 78 and 80, each having an end secured in portion 72, extend through corresponding openings in portions 74 and 76 to align all three portions 72, 74 and 76 during assembly. This construction allows the invention to be readily disassembled for cleaning and fluid sterilization. Although housing 52 may have any suitable construction, it is preferably disassemblable.

Obviously, other embodiments and modifications of the present invention will occur readily to those of ordinary skill in the art in view of these teachings. Therefore, this invention is to be limited only by the following claims, which include all such other embodiments and modifications when viewed in conjunction with the above specification and accompanying drawings.

What is claimed is:

1. A blade injector for mounting a blade having an aperture on a surgical instrument head having a groove, comprising:

a housing having a cavity elongated along an axis for retaining said blade; and said elongated cavity having a channel angled with respect to said axis for guiding said instrument head.

2. The blade injector recited in claim 1, wherein said housing has a plurality of elongated cavities for retaining a plurality of blades.

3. The blade injector recited in claim 1, further comprising a seal on said housing covering an end of said elongated cavity.

4. The blade injector recited in claim 1, wherein said seal is breakable.

5. The blade injector recited in claim 1, further comprising a handle.

6. The method for mounting a blade having an aperture on a surgical instrument head having a groove recited in claim 5, further comprising the step of unsealing a seal on said housing.

7. The method for mounting a blade having an aperture on a surgical instrument head having a groove recited in claim 6, wherein said step of unsealing a seal comprises the step of puncturing said seal with said surgical instrument head.

8. A method for mounting a blade having an aperture on a surgical instrument head having a groove, comprising the steps of:

providing a housing having a cavity elongated along an axis for retaining said blade, said elongated cavity having a channel angled with respect to said axis for guiding said surgical instrument;

inserting said surgical instrument head into said cavity in a direction substantially parallel to said angled channel;

inserting said surgical instrument head into said aperture, said head remaining substantially parallel to said angled channel until said groove has engaged said blade; and withdrawing said surgical instrument from said cavity when said head is fully engaged in said blade.

* * * * *